(12) United States Patent
Mastromatteo et al.

(10) Patent No.: US 7,906,321 B2
(45) Date of Patent: Mar. 15, 2011

(54) INTEGRATED SEMICONDUCTOR MICROREACTOR FOR REAL-TIME MONITORING OF BIOLOGICAL REACTIONS

(75) Inventors: Ubaldo Mastromatteo, Bareggio (IT); Flavio Villa, Milan (IT); Gabriele Barlocchi, Cornaredo (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 779 days.

(21) Appl. No.: 11/009,171

(22) Filed: Dec. 10, 2004

(65) Prior Publication Data
US 2005/0176037 A1   Aug. 11, 2005

(30) Foreign Application Priority Data
Dec. 12, 2003  (EP) .................................... 03425800

(51) Int. Cl.
*C12M 1/34*  (2006.01)
*C12M 3/00*  (2006.01)
(52) U.S. Cl. ........ 435/288.7; 435/287.2; 438/1; 422/130
(58) Field of Classification Search .................. 422/130; 435/288.7
See application file for complete search history.

(56) References Cited

U.S. PATENT DOCUMENTS

| | | | |
|---|---|---|---|
| 4,993,143 A | 2/1991 | Sidner et al. | |
| 5,429,734 A | 7/1995 | Gajar et al. | |
| 5,637,469 A | 6/1997 | Wilding et al. | |
| 5,639,423 A | 6/1997 | Northrup et al. | |
| 5,922,591 A | 7/1999 | Anderson et al. | |
| 5,939,312 A | 8/1999 | Baier et al. | |
| 5,942,443 A | 8/1999 | Parce et al. | |
| 6,046,056 A | 4/2000 | Parce et al. | |
| 6,093,330 A * | 7/2000 | Chong et al. | 216/2 |
| 6,168,948 B1 | 1/2001 | Anderson et al. | |
| 6,207,031 B1 * | 3/2001 | Adourian et al. | 204/451 |
| 6,261,431 B1 | 7/2001 | Mathies et al. | |
| 6,267,858 B1 | 7/2001 | Parce et al. | |
| 6,376,291 B1 | 4/2002 | Barlocchi et al. | |
| 6,403,367 B1 | 6/2002 | Cheng et al. | |
| 6,490,034 B1 * | 12/2002 | Woias et al. | 356/246 |
| 6,583,044 B2 * | 6/2003 | Bahl et al. | 438/619 |
| 6,716,661 B2 * | 4/2004 | Zou et al. | 438/49 |

(Continued)

FOREIGN PATENT DOCUMENTS
DE   19647644 A   5/1998
(Continued)

OTHER PUBLICATIONS
Svanvik N. et al., Detection of PCR products in Real Time Using Light-up Probes, Analytical Biochemistry 287, 179-182 (2000).
(Continued)

*Primary Examiner* — William H Beisner
*Assistant Examiner* — Michael Hobbs
(74) *Attorney, Agent, or Firm* — Boulware & Valoir

(57) ABSTRACT

An integrated semiconductor chemical microreactor for real-time polymerase chain reaction (PCR) monitoring, has a monolithic body of semiconductor material; a number of buried channels formed in the monolithic body; an inlet trench and an outlet trench for each buried channel; and a monitoring trench for each buried channel, extending between the inlet and outlet trenches thereof from the top surface of the monolithic body to the respective buried channel. Real-time PCR monitoring is carried out by channeling light beams into the buried channels, possibly through one of the inlet or outlet trenches, whereby the light beams impinge on the fluid therein and collecting the emergent light coming out from the monitoring trench.

17 Claims, 4 Drawing Sheets

U.S. PATENT DOCUMENTS

| | | |
|---|---|---|
| 6,770,471 B2 | 8/2004 | Barlocchi et al. |
| 2001/0029036 A1 * | 10/2001 | Landers et al. ............ 435/91.1 |
| 2001/0036672 A1 | 11/2001 | Anderson et al. |
| 2002/0017660 A1 | 2/2002 | Villa et al. |
| 2002/0022261 A1 | 2/2002 | Anderson et al. |
| 2002/0045244 A1 | 4/2002 | Barlocchi et al. |
| 2002/0055167 A1 | 5/2002 | Pourahmadi et al. |
| 2002/0060156 A1 | 5/2002 | Mathies et al. |
| 2002/0068334 A1 | 6/2002 | Carrino et al. |
| 2002/0068357 A1 | 6/2002 | Mathies et al. |
| 2002/0094533 A1 * | 7/2002 | Hess et al. ..................... 435/6 |
| 2002/0097900 A1 | 7/2002 | Arena et al. |
| 2002/0145121 A1 | 10/2002 | Huhn et al. |
| 2002/0150933 A1 | 10/2002 | Ehricht et al. |
| 2003/0057199 A1 | 3/2003 | Villa et al. |
| 2003/0148401 A1 * | 8/2003 | Agrawal et al. ............... 435/7.9 |
| 2004/0132059 A1 | 7/2004 | Scurati et al. |
| 2004/0141856 A1 | 7/2004 | Scurati |

FOREIGN PATENT DOCUMENTS

| | | |
|---|---|---|
| EP | 1 043 770 | 10/2000 |
| EP | 1 123 739 | 8/2001 |
| EP | 1 130 631 A1 | 9/2001 |
| EP | 1 161 985 A1 | 12/2001 |
| IT | 1 193 214 A1 * | 4/2002 |
| WO | WO 01/20309 A | 3/2001 |
| WO | WO 02/22265 A | 3/2002 |
| WO | WO 03/016075 A | 2/2003 |

OTHER PUBLICATIONS

Zhang, N., Automated and Integrated System for Thigh-Throughput DNA Genotyping Directly from Blood, Analytical Chemistry, Mar. 15, 1999, pp. 1138-1145, vol. 71(6).

Search report, EP 03 425 800 filed Jul. 13, 2004.

* cited by examiner

INTEGRATED SEMICONDUCTOR MICROREACTOR FOR REAL-TIME MONITORING OF BIOLOGICAL REACTIONS

PRIOR RELATED APPLICATIONS

This application claims priority to application EP 03425800.4 filed on Dec. 12, 2003.

BACKGROUND OF THE INVENTION

Typical procedures for analyzing biological materials, such as nucleic acid, involve a variety of operations starting from raw material. These operations may include various degrees of cell purification, lysis, amplification or purification, and analysis of the resulting amplification or purification product.

As an example, in DNA-based blood tests the samples are often purified by filtration, centrifugation or by electrophoresis so as to eliminate all the non-nucleated cells. Then, the remaining white blood cells are lysed using chemical, thermal or biochemical means in order to liberate the DNA to be analyzed.

Next, the DNA is denatured by thermal, biochemical or chemical processes and amplified by an amplification reaction, such as PCR (polymerase chain reaction), LCR (ligase chain reaction), SDA (strand displacement amplification), TMA (transcription-mediated amplification), RCA (rolling circle amplification), and the like. The amplification step allows the operator to avoid purification of the DNA being studied because the amplified product greatly exceeds the starting DNA in the sample.

The procedures are similar when RNA is to be analyzed, but more emphasis is placed on purification or other means to protect the labile RNA molecule. RNA is usually copied into DNA (cDNA) and then the analysis proceeds as described for DNA.

Finally, the amplification product undergoes some type of analysis, usually based on sequence or size or some combination thereof. In an analysis by hybridization, for example, the amplified DNA is passed over a plurality of detectors made up of individual oligonucleotide probes that are anchored, for example, on electrodes. If the amplified DNA strands are complementary to the probes, stable bonds will be formed between them and the hybridized detectors can be read by a wide variety of means, including optical, electrical, magnetic, mechanical or thermal means.

Other biological molecules are analyzed in a similar way, but typically molecule purification is substituted for amplification and detection methods vary according to the molecule being detected. For example, a common diagnostic involves the detection of a specific protein by binding to its antibody or by an enzymatic reaction of some sort. Lipids, carbohydrates, drugs and small molecules from biological fluids are processed in similar ways.

It is also known that the most sensitive method to determine the amount of a specific DNA in a sample is the so-called real-time PCR, where the amount of product is measured during ongoing amplification.

During the past few years a number of technologies for simultaneous amplification and detection have been developed. In the simplest assay, the PCR product is detected through the binding of double-strand DNA specific dyes. These kind of dyes have no fluorescence of their own, but become intensively fluorescent when they bind to nucleic acids. However, most are not sequence specific, but will bind to any double-stranded nucleic acid, including the commonly formed, but diagnostically irrelevant, primer-dimer.

A number of oligonucleotide-dye conjugates have been developed that bind via the oligomer to internal DNA sequences and thus allow sequence specific detection. These labels are useful for real-time monitoring of multiplex amplification.

Recently, a new probe for sequence specific detection of target DNA in solution has been proposed (Svanvik N., et al., Detection of PCR Products in Real Time Using Light-up Probes, Analytical Biochemistry 287, 179-182 (2000)). The probe is a peptide nucleic acid to which an asymmetric dye is tethered. Upon sequence specific probe hybridization, the dye also binds to the target DNA, which results in a large increase in fluorescence.

The discussion herein has been simplified by focusing on nucleic acid analysis, in particular DNA amplification, as an example of a biological molecule that can be analyzed using the devices of the invention. However, as described above, the invention can be used for real time monitoring of any chemical or biological test.

Recently, monolithic integrated devices of semiconductor material have been proposed, able to process small fluid quantities with a controlled reaction, and at a low cost (see publications EP161985, EP123739, EP193214, US20030057199, applications EP 03103421.8 and EP 03103422.6, both filed on Sep. 17, 2003, all in the name of the present Applicant).

These devices comprise a semiconductor material body accommodating buried channels that are connected, via input and output trenches, to input and output reservoirs, respectively, to which the fluid to be processed is supplied, and from which the fluid is collected at the end of the reaction. Above the buried channels, heating elements and thermal sensors are provided to control the thermal conditions of the reaction. In one embodiment, the output reservoir also contains detection electrodes that are provided for examining the reacted fluid.

An ever-increasing market demand exists for integrated semiconductor chemical microreactors designed to easily allow real-time monitoring of the reaction occurring within the device.

The aim of the present invention is therefore to provide an integrated semiconductor chemical microreactor for real-time amplification monitoring which meets such a market demand.

SUMMARY OF THE INVENTION

The present invention relates to an integrated semiconductor chemical microreactor for real-time monitoring of biological reactions, for example amplification reactions. According to the present invention, a microreactor and a process for manufacturing the same are provided. Generally speaking, the microreactor has buried channels within the body of the semiconductor, which are connected to the surface though inlet and outlet openings and/or reservoirs. At some point along the buried channel—either midway or towards the end—an additional opening is made. The opening is covered with transparent material, e.g., resist or glass, which allows visual monitoring of the contents, but protects same from contamination and fluid loss. The walls of the channels are conveniently angled to allow reflection of light.

Also provided are a method and a system for real-time monitoring a desired product within a fluid.

For a better understanding of the present invention, a preferred embodiment thereof is now described, simply as non-limiting example, with reference to the attached drawings, wherein:

DETAILED DESCRIPTION OF THE INVENTION

Figure 1:
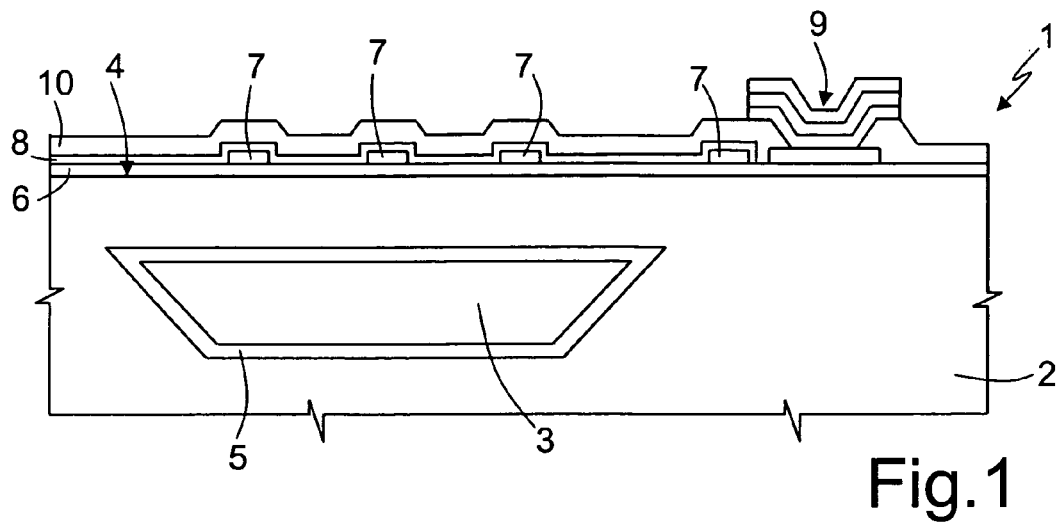
FIGS. 1-5, 7 and 8 show cross-sections of a semiconductor material wafer in successive manufacturing steps of the integrated semiconductor chemical microreactor according to the invention.

FIG. 1 shows a cross-section of a semiconductor material wafer after some initial manufacture steps of the integrated semiconductor chemical microreactor of the invention have been carried out.

In particular, FIG. 1 shows a wafer 1 comprising a monolithic semiconductor body 2, typically of monocrystalline silicon, in which a number of buried channels 3 are formed which extend parallel to, and a distance from a top surface 4 of the semiconductor body 2.

The buried channels 3 are preferably coated with an insulating material 5, such as silicon oxide or TEOS (tetra-ethyl orthosilicate) formed by CVD (chemical vapor deposition). Any material to remove or cover the reactive surface will do.

In the example shown in FIG. 1, the buried channels 3 have an isosceles trapezium longitudinal cross-section with longitudinal ends defined by sloping walls. They have an average width of approximately 200 µm, a height of approximately 150 µm and a length of approximately 10 mm. Furthermore, the buried channels 3 are arranged at a depth of about 10 µm from the surface 4 and are divided in groups, the buried channels 3 in each group being arranged at a distance of approximately 50 µm from one another and the groups being arranged at a distance of approximately 1 mm from one another.

The buried channels 3 may for example be formed as described in EP043770 and EP130631, both in the name of the present Applicant.

A first insulating layer 6, for example of silicon dioxide, is formed on the surface 4 of the semiconductor body 2.

A number of polycrystalline-silicon heating elements 7 are then formed on the first insulating layer 6. Preferably, the heating elements 7 are arranged in rows and extend substantially equispaced over the buried channels 3, but not over the longitudinal ends of the buried channels 3, where an inlet trench and an outlet trench of the channels 3 are to be formed, as described hereinafter.

Contact regions (not shown), for example of aluminum, electrically contact two opposite ends of the heating elements 7 to enable passage of electric current through the heating elements 7 and heating of the underlying area.

A second insulating layer 8, for example of silicon dioxide, is formed on the first insulating layer 6, over the area occupied by the buried channels 3, and completely covers the heating elements 7.

A sensing electrode 9 is formed on the first insulating layer 6 in the area not covered by the second insulating layer 8, laterally staggered with respect to the buried channels 3, and is made up of a multilayer, for example of aluminum, titanium, nickel and gold, in a per se known manner and hence not described in detail herein.

A third insulating layer 10, for example of TEOS, is formed on the second insulating layer 8 and has an opening through which the sensing electrode 9 protrudes.

The initial manufacture steps previously described are the same as, or similar to those disclosed in the above-referenced EP161985 and EP123739.

Figure 2:
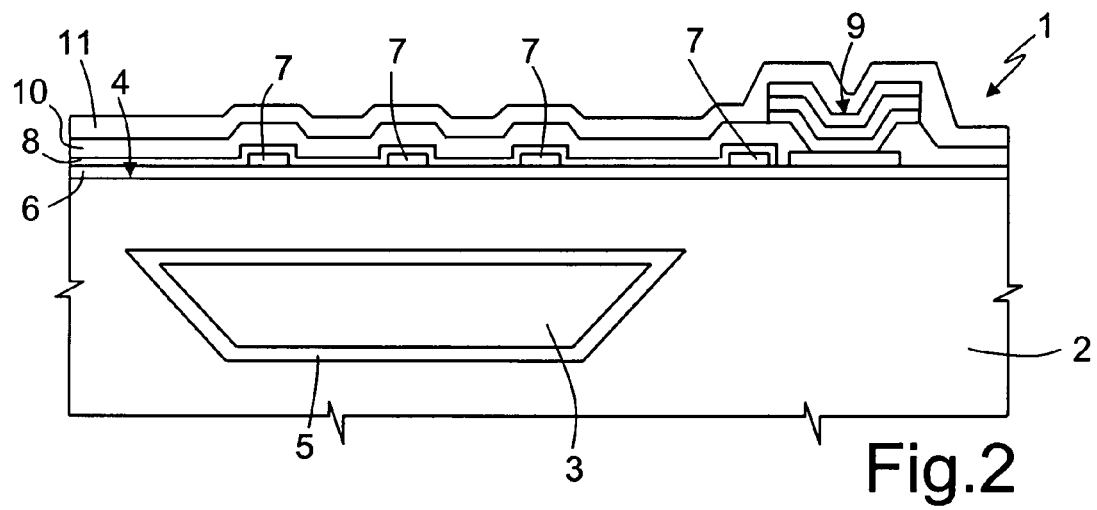
Figure 3:
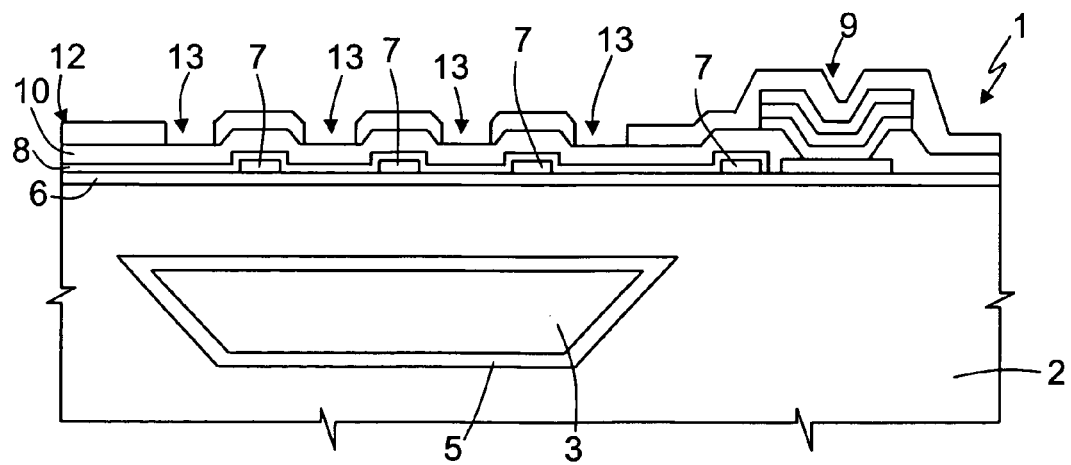

A resist layer 11 is then deposited on the third insulating layer 10 (FIG. 2) and defined to form a grid-shaped resist mask 12 over the buried channels 3 (FIG. 3).

In particular, the grid-shaped resist mask 12 has openings 13 which may have any form, for example square, rectangular, hexagonal, polygonal or circular, and which are arranged in rows and extend substantially equispaced over the buried channels 3 so as to protect portions of the third insulating layer 10 over the heating elements 7 and to leave uncovered portions of the third insulating layer 10 between the heating elements 7.

Figure 4:
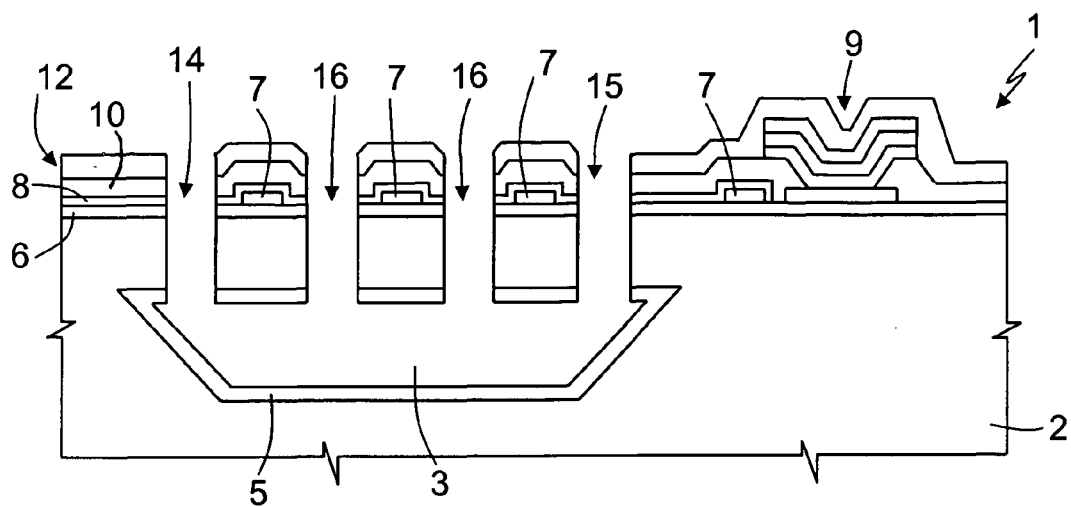

A dry etch is then carried out, thus forming trenches in the semiconductor body 2 at the openings 13 of the grid-shaped resist mask 12, which trenches extend in depth from the surface 4 of the semiconductor body 2 to the buried channels 3, thus putting the buried channels 3 in communication with the exterior (FIG. 4). In particular, the dry etch forms, for each buried channel 3, an inlet trench 14 and an outlet trench 15 extending at the longitudinal ends of the buried channel 3 defined by the sloping walls thereof. There are also a number of monitoring trenches 16 distinct from the inlet and outlet trenches 14, 15 and extending over the buried channel 3, between the heating elements 7 and between the inlet and outlet trenches 14, 15.

Figure 5:
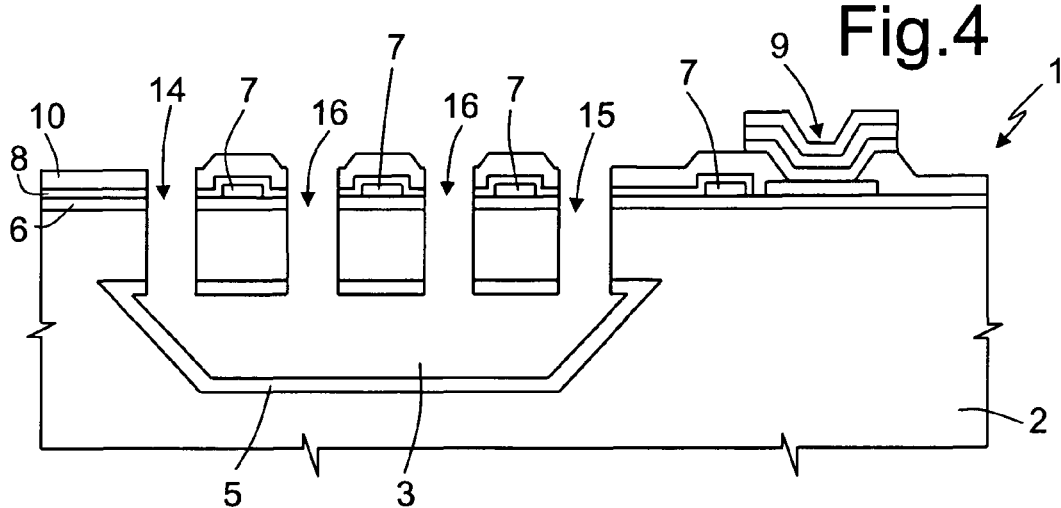
Figure 6:
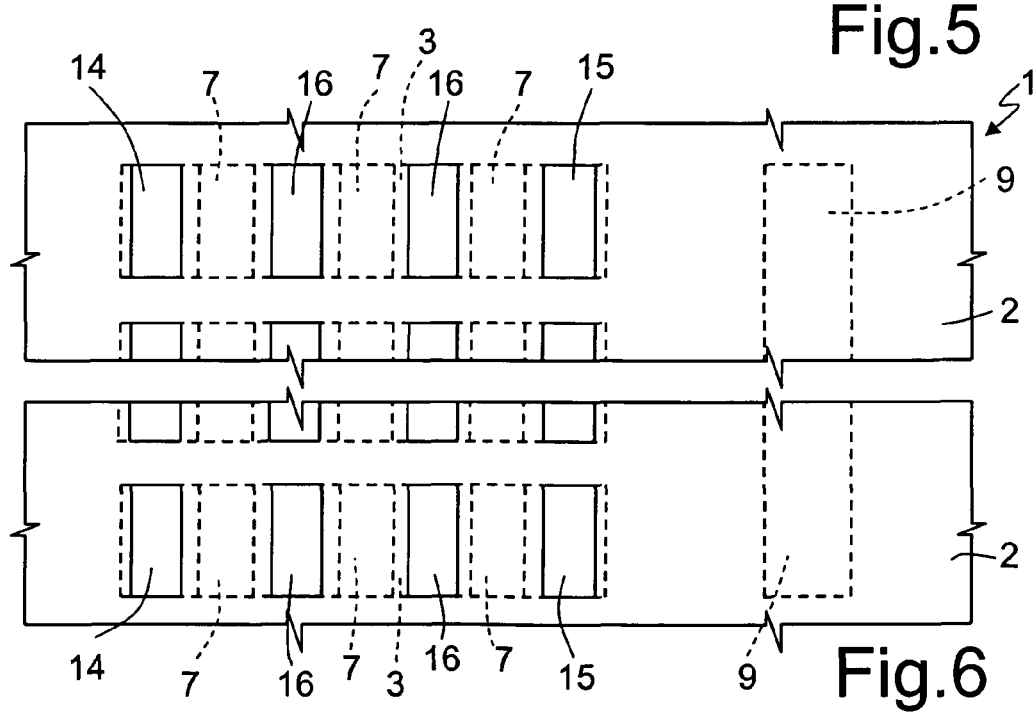
FIG. 6 shows a top plan view of a semiconductor material wafer in an intermediate manufacturing step of the integrated semiconductor chemical microreactor according to the invention.

The grid-shaped resist mask 12 is then removed, thus obtaining the structure shown in cross-section in FIG. 5, and, in plan view, in FIG. 6.

Figure 7:
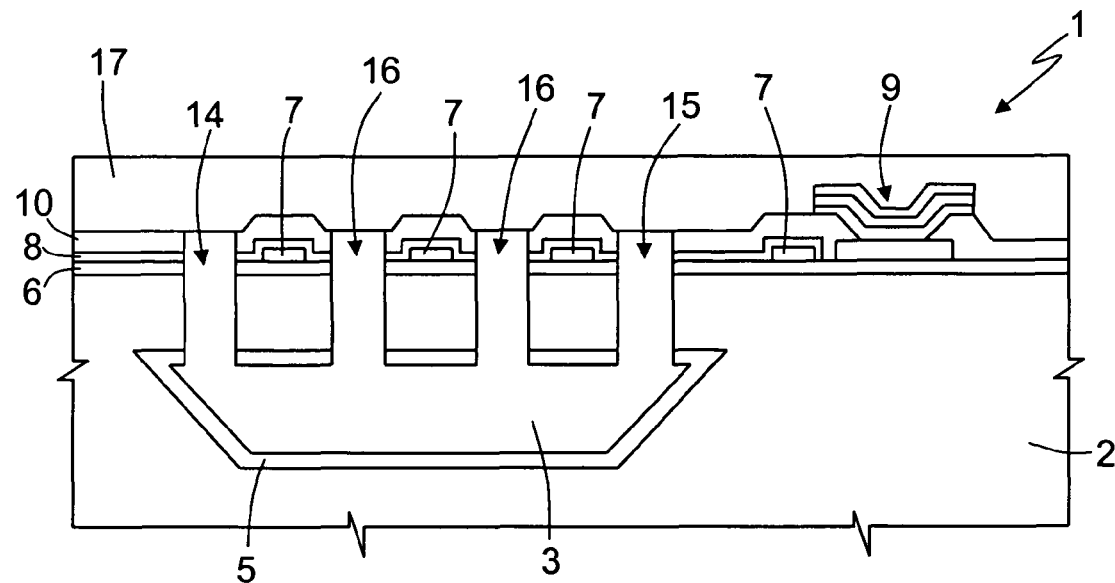

A photosensitive dry resist layer 17 with a thickness of about 10 µm is then formed on the third insulating layer 10 (FIG. 7). Conveniently, the photosensitive dry resist layer 17 may be formed by laminating a thicker photosensitive dry resist film generally sold in the form of a roll with different sizes and thicknesses, applying the laminated photosensitive dry resist film to the third insulating layer 10 by thermocompression at a temperature of between 105° C. and 118° C., and then cutting the photosensitive dry resist film to adapt its shape to that (typically circular) of the wafer 1.

Figure 8:
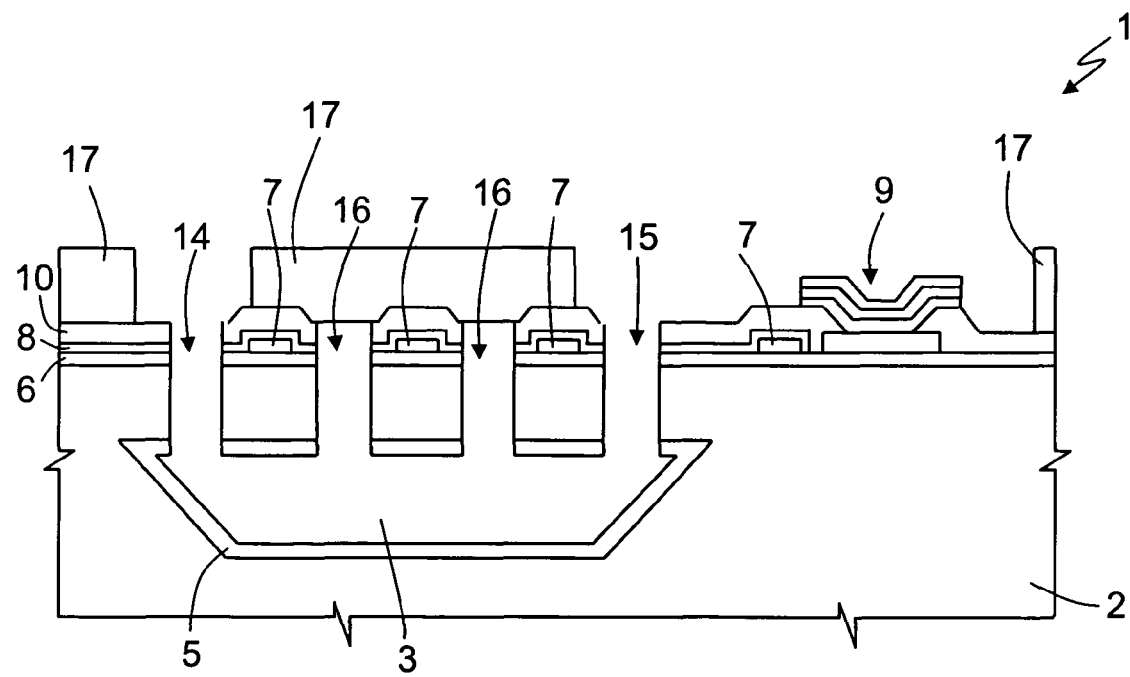

Using a mask (not shown), the photosensitive dry resist layer 17 is then exposed, developed and etched to remove portions of the photosensitive dry resist layer 17 only over the inlet and outlet trenches 14, 15, where an inlet reservoir and an outlet reservoir are to be formed, as described hereinafter. This leaves the areas over the buried channels 3 completely covered to prevent the processed fluid in the buried channels 3 from coming out therefrom through the monitoring trenches 16 (FIG. 8).

Figure 9:
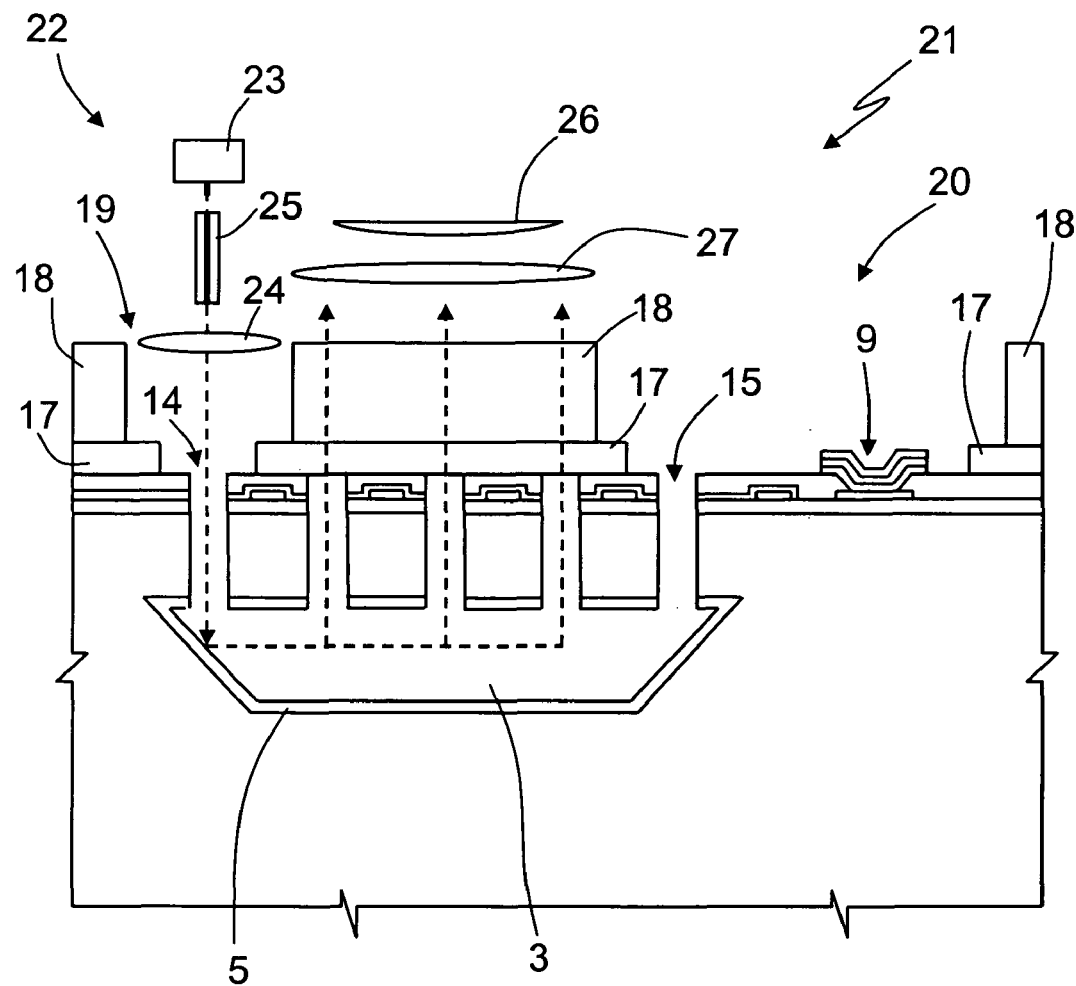
FIG. 9 shows a cross-section of an integrated semiconductor chemical microreactor according to the invention.

In order to have an appropriate volume of the inlet and outlet reservoirs 19, 20, a glass plate 18 having the same dimension as the wafer 1 is then bonded to the photosensitive dry resist layer 17, the glass plate 18 having been previously appropriately defined to form the inlet and outlet reservoirs 19, 20 over the inlet and outlet trenches 14, 15, using known techniques, for example by means of a pressurized sandblast, thus obtaining the structure shown in FIG. 9.

In particular, the inlet reservoir 19 is formed as an extension of the inlet trenches 14 and is connected to all the first ends of the buried channels 3. Whereas the outlet reservoir 20 is formed as an extension of the outlet trenches 15 close to the sensing electrode 9 and is connected to all the second ends of the buried channels 3, thus leaving the sensing electrode 9 exposed.

Preferably, the reservoirs 19, 20 have a length (in a direction perpendicular to the plane of FIG. 9) of approximately 6-10 mm; the inlet reservoir 19 has a width (in a horizontal direction in FIG. 9) of between 300 µm and 1.5 mm, preferably approximately 1 mm, and a thickness (in a vertical direction in FIG. 9) preferably comprised between 300 µm and 400 µm, so as to yield a volume of at least 1 mm$^3$. The outlet reservoir 20 has a width of between 1 and 4 mm, preferably of approximately 2.5 mm, whereas the other dimensions are the same as the inlet reservoir.

The structure shown in FIG. 9 defines the integrated semiconductor chemical microreactor according to the invention, designated as a whole by 21 in FIG. 9, which allows the amplification process to be monitored in real-time.

In one method of use, the fluid containing the DNA to be amplified and a fluorescent reporter are introduced into the buried channels 3 via the inlet trenches 14. In our example, the reporter emits light with a specific wavelength, generally 530 nm, when stimulated by light of an appropriate wavelength, generally 470 nm, on condition that it is bound to a double-strand nucleic acid.

The fluid is then heated within the buried channels 3 by means of the heating elements 7 according to the thermocycles needed for amplification. Ultimately, the treated fluid (amplicon) may be extracted from the buried channels 3 via the outlet trenches 15.

However, the amount of DNA within the buried channels 3 may also be real-time monitored during ongoing amplification through the monitoring trenches 16.

In particular, according to the invention, a monochromatic light beam, indicated in FIG. 9 by a dashed line, is channeled into each inlet trench 14, is deflected into the buried channel 3 by the sloping wall thereof facing the inlet trench 14, and impinges on the fluid within the buried channel 3.

When the monochromatic light beam impinges on the fluid within the buried channel 3, the fluid becomes intensively fluorescent and the signal is a function of the DNA concentration at that moment in time. Continued measurements will allow the determination of amplification rate.

Therefore, by collecting the light beams emitted by the stimulated fluid and coming out from the monitoring trenches 16 over each buried channel 3, indicated in FIG. 9 by dashed lines, it possible to real-time monitor the amount of DNA in the buried channel 3 during ongoing amplification.

The monochromatic light beam channeled into the inlet trench 14 of each buried channel 3 may for example be generated by an external input optical system. This is shown in FIG. 9 and designated as a whole by 22. It either consists of a single laser light source (not shown) or a white light source 23, an appropriate filter lens system 24 to generate and direct monochromatic light beams at the inlet trenches 14, and an optical fiber system 25 channeling the white light beams onto the filter lens system 24.

Similarly, the light emitted by the stimulated fluid and coming out from the monitoring trenches 16 may for example be collected and channeled to a photo detector 26. For example, a Single Photon Avalanche Diode (SPAD) may be employed by means of an appropriate focusing lens system 27, and the signal then appropriately processed.

The advantages of the integrated semiconductor chemical microreactor of the invention emerge clearly from the foregoing description.

In particular, the integrated semiconductor chemical microreactor of the invention is simple to manufacture and allows the PCR process to be easily real-time monitored during ongoing amplification.

From the foregoing it will be appreciated that, although a specific embodiment of the invention has been described herein for purposes of illustration, various modifications may be made without deviating from the spirit and scope of the invention, as defined by the appended claims.

For example, the monitoring of the ongoing DNA amplification may be carried out also by channeling the monochromatic light beam into the outlet trenches 15 of the buried channels 3, instead of into the inlet trenches 14.

Furthermore, optical inspection of the buried channels 3 to real-time monitor the PCR process during ongoing amplification may also be carried out from the back of the chip, i.e. by forming monitoring trenches arranged below the buried channels 3 and extending from the bottom surface of the body 2 to the buried channels 3 and then by filling the monitoring trenches with a transparent material, for example a resist layer, to prevent the processed fluid into the buried channels 3 from coming out therefrom through the monitoring trenches. In this embodiment, appropriate light channeling means have to be provided to channel the light beams coming from the monitoring trenches towards a photo detector.

Moreover, the microreactor may also be made of materials different than semiconductor material, for example ceramic.

Further, the real-time monitoring system may be combined with other features convenient for the application of interest, such as a micropump, sample pre-treatment chamber, lysis chamber, and the like.

Lastly, as initially discussed, the present invention may be used for real-time monitoring of other fluids during ongoing processing.

The invention claimed is:

1. A microreactor comprising:
   a. a semiconductor monolithic body;
   b. at least one buried channel in said monolithic body and a plurality of heating elements above said buried channel;
   c. said semiconductor monolithic body having openings extending through a top surface of the semiconductor monolithic body into said buried channel to fluidly connect an exterior of said semiconductor monolithic body into said buried channel;
   d. said openings comprising an inlet opening and an outlet opening, said inlet and outlet openings at opposite ends of said buried channel, and a plurality of monitoring openings therebetween and configured to allow optical inspection of said buried channel;
   e. said buried channel further comprising a sloping wall configured to reflect light entering the inlet or outlet openings into said buried channel;
   f. wherein each of said monitoring openings is positioned between a pair of said plurality of heating elements;
   g. a first transparent material layer arranged to close said monitoring openings;
   h. a second transparent material layer of glass over said first transparent material layer;
   i. at least one inlet reservoir formed in said first and second transparent material layers above said inlet opening; and
   j. at least one outlet reservoir formed in said first and second transparent material layers above said outlet opening.

2. The microreactor of claim 1, wherein said first transparent material layer is a dry resist layer.

3. A process for manufacturing a microreactor comprising:
   a. forming at least one buried channel having a sloping wall in a semiconductor monolithic body;
   b. forming openings extending through a top surface of the semiconductor monolithic body into said buried channel to fluidly connect an exterior of said semiconductor monolithic body into said buried channel, so that light entering said openings is reflected by said sloping wall into said buried channel, and wherein said openings are an inlet opening and an outlet opening at opposite ends of the buried channel, and a plurality of monitoring openings therebetween;
c. forming a plurality of heating elements above said buried channel, such that each monitoring opening is between a pair of heating elements;
d. forming first and second transparent material layers arranged to close said monitoring openings;
e. forming at least one inlet reservoir in said first and second transparent material layers above said inlet opening; and
f. forming at least one outlet reservoir in said first and second transparent material layers above said outlet opening.

4. The process of claim 3, wherein forming said openings comprises:
a. forming a resist mask over said buried channel;
b. dry etching said monolithic body.

5. A method for real-time monitoring a desired product within a fluid in a microreactor, said microreactor comprising:
a. a monolithic body;
b. at least one buried channel having a sloping wall formed inside said monolithic body and containing a fluid; and
c. an inlet opening and an outlet opening formed at opposite ends of said buried channel and extending through a top surface of said monolithic body into said buried channel to fluidly connect an exterior of said monolithic body into said buried channel;
d. a plurality of monitoring openings extending through a top surface of said monolithic body into said buried channel to fluidly connect an exterior of said monolithic body into said buried channel and configured to allow optical inspection of said fluid;
e. a plurality of heaters formed on the monolithic body, over the buried channel, wherein each of said monitoring openings are positioned between a pair of said plurality of heaters;
f. a first and a second transparent material layer arranged to close said monitoring openings;
g. at least one inlet reservoir formed in said first and second transparent material layers above said inlet opening; and
h. at least one outlet reservoir formed in said first and second transparent material layers above said outlet opening;
said method comprising:
i) channeling a light beam into said buried channel, whereby said light beam reflects off said sloping wall into said buried channel; and
ii) collecting and processing a one or more light beams emerging from said monitoring openings.

6. The method of claim 5, wherein said fluid within said buried channel contains a fluorescent reporter and wherein said monochromatic light beam has a wavelength that causes said fluorescent reporter to fluoresce when it impinges thereon.

7. The method of claim 5, wherein said light beam is a monochromatic light beam.

8. The method of claim 5, wherein channeling a light beam comprises:
a. generating a white light beam; and
b. sending said white light beam to a filter.

9. The method of claim 5, wherein said fluid is a biological fluid, a nucleic acid, or DNA.

10. A system for real-time monitoring a desired product within a fluid, comprising:
a. a microreactor including:
i. a monolithic body;
ii. at least one buried channel formed in said monolithic body and containing said fluid; and
iii. inlet and outlet openings formed at opposite ends of said buried channel and extending through a top surface of said monolithic body into said buried channel to fluidly connect an exterior of said monolithic body into said buried channel;
iv. a plurality of monitoring openings extending through said top surface of said monolithic body into said buried channel to fluidly connect an exterior of said monolithic body into said buried channel;
v. a plurality of heaters formed on the monolithic body, over the buried channel, wherein each of said monitoring openings is positioned between a pair of said heaters;
vi. a first and a second transparent material layer arranged to close said monitoring openings;
vii. at least one inlet reservoir formed in said first and second transparent material layers above said inlet opening; and
viii. at least one outlet reservoir formed in said first and second transparent material layers above said outlet opening;
b. a light source generating a light beam arranged over said inlet or outlet openings;
c. a light path extending between said light source and said buried channel, whereby said light beam is channeled into said buried channel and impinges on said fluid within said buried channel; and
d. a light processing arrangement arranged over said monitoring openings for collecting and processing an emergent light emerging from said monitoring opening.

11. The system of claim 10, wherein said light channeling arrangement comprises a deflecting device for deflecting said light beam from said inlet opening into said buried channel.

12. The system of claim 10, wherein said deflecting device is defined by a sloping wall at an end of said buried channel facing said inlet opening.

13. The system of claim 10, wherein said fluid within said buried channel contains a fluorescent reporter and wherein said monochromatic light beam has a wavelength that causes said fluorescent reporter to fluoresce when it impinges thereon.

14. The method of claim 10, wherein said fluid comprises a biological material or nucleic acid or DNA.

15. The microreactor of claim 1, further comprising insulating layer coating said buried channel, wherein said monitoring opening passes through said insulating layer.

16. The process of claim 3, comprising simultaneously forming said inlet opening, outlet opening and at least one monitoring opening.

17. A microreactor comprising:
a. a semiconductor monolithic body;
b. at least one buried channel in said monolithic body, said monolithic body defining upper, lower and side walls of the buried channel and said walls defining said buried channel;
c. a plurality of heating elements above said buried channel,
d. said monolithic body having openings extending through a top surface of the monolithic body through said upper wall of said buried channel to fluidly connect an exterior of said monolithic body to an interior of said buried channel;
e. said openings comprising an inlet opening and an outlet opening at opposite ends of said buried channel, and a plurality of monitoring openings therebetween and configured to allow optical inspection of said buried channel;
f. said buried channel further comprising a sloping wall configured to reflect light entering the inlet or outlet openings into said buried channel;
g. each of said plurality of monitoring openings are positioned between a pair of said plurality of heating elements;
h. a first and a second transparent material layer arranged to close said monitoring openings;
i. at least one inlet reservoir formed in said first and second transparent material layers above said inlet opening; and
j. at least one outlet reservoir formed in said first and second transparent material layers above said outlet opening; and
k. a sensing electrode arranged in the outlet reservoir.

* * * * *